(12) United States Patent
Walder et al.

(10) Patent No.: US 7,758,618 B2
(45) Date of Patent: *Jul. 20, 2010

(54) PEDICLE SCREW FOR INTERVERTEBRAL SUPPORT ELEMENTS

(75) Inventors: Reto Walder, Pfungen (CH); Reto Braunschweiler, Neftenbach (CH)

(73) Assignee: Zimmer GmbH, Winterthur (CH)

( * ) Notice: Subject to any disclaimer, the term of this patent is extended or adjusted under 35 U.S.C. 154(b) by 250 days.

This patent is subject to a terminal disclaimer.

(21) Appl. No.: 12/128,744

(22) Filed: May 29, 2008

(65) Prior Publication Data

US 2008/0234734 A1    Sep. 25, 2008

Related U.S. Application Data

(63) Continuation of application No. 11/565,825, filed on Dec. 1, 2006, now Pat. No. 7,611,518, which is a continuation of application No. 09/956,055, filed on Sep. 18, 2001.

(30) Foreign Application Priority Data

Sep. 18, 2000    (EP)    .................................. 00810845

(51) Int. Cl.
    *A61B 17/70*    (2006.01)
    *A61B 17/04*    (2006.01)
(52) U.S. Cl. .................. 606/246; 606/301; 606/305
(58) Field of Classification Search .................. 606/254, 606/264, 266, 59, 246, 279, 261, 257, 267, 606/907, 86 A, 301, 305
    See application file for complete search history.

(56) References Cited

U.S. PATENT DOCUMENTS 5,042,982 A * 8/1991 Harms et al. ................ 606/256

| 5,282,863 A | 2/1994 | Burton |
| 5,375,823 A | 12/1994 | Navas |

(Continued)

FOREIGN PATENT DOCUMENTS

EP    0669109 A1    8/1995

(Continued)

*Primary Examiner*—Pedro Philogene
(74) *Attorney, Agent, or Firm*—Crompton, Seager & Tufte, LLC.

(57) ABSTRACT

The pedicle screw (1) for intervertebral support elements (3) consists of a shaft (10) and a head (2) comprising at least two parts (20, 22). The head is formed as a securing means for at least one support element (3). Each support element consists of a piece of a cable-like band (31) and a cylindrical support body (30) with an axial lumen (31″ containing the band. The band is securable outside end surfaces (32) of the support body in the head. The head is formed with a contact surface (23) via which a pressure stress can be exerted on the support body in the band direction, and indeed using the band and in cooperation with a further pedicle screw. A part (20) of the head (2), which is firmly connected to the shaft (10) at the one end of the latter, contains a base groove (21) which is oriented transversally to the shaft and into which the part of the band (31) to be secured or a connecting piece (292) which contains the band can be introduced during the securing of the support element (3) by means of a translatory movement in the direction of the shaft and fixed there.

22 Claims, 5 Drawing Sheets

U.S. PATENT DOCUMENTS

| | | | |
|---|---|---|---|
| 5,520,689 A | 5/1996 | Schlapfer et al. | |
| 5,540,688 A | 7/1996 | Navas | |
| 5,562,660 A * | 10/1996 | Grob | 606/258 |
| 5,611,800 A | 3/1997 | Davis et al. | |
| 5,643,260 A | 7/1997 | Doherty | |
| 5,725,582 A | 3/1998 | Bevan et al. | |
| 5,961,516 A | 10/1999 | Graf | |
| 6,053,917 A | 4/2000 | Sherman et al. | |
| 6,090,111 A | 7/2000 | Nichols | |
| 6,110,172 A | 8/2000 | Jackson | |
| 6,139,549 A | 10/2000 | Keller | |
| 6,241,730 B1 | 6/2001 | Alby | |
| 6,258,090 B1 | 7/2001 | Jackson | |
| 6,280,442 B1 | 8/2001 | Barker et al. | |
| 6,290,700 B1 * | 9/2001 | Schmotzer | 606/263 |
| 6,296,642 B1 | 10/2001 | Morrison et al. | |
| 6,361,535 B2 | 3/2002 | Jackson et al. | |
| 6,986,771 B2 | 1/2006 | Paul et al. | |
| 6,989,011 B2 | 1/2006 | Paul et al. | |
| 7,326,210 B2 | 2/2008 | Jahng et al. | |
| 7,611,518 B2 * | 11/2009 | Walder et al. | 606/86 A |
| 2002/0035366 A1 | 3/2002 | Walder et al. | |
| 2005/0085815 A1 | 4/2005 | Harms et al. | |
| 2005/0124991 A1 | 6/2005 | Jahng | |
| 2005/0143737 A1 | 6/2005 | Pafford et al. | |
| 2005/0154390 A1 | 7/2005 | Biedermann et al. | |
| 2005/0203513 A1 | 9/2005 | Jahng et al. | |
| 2006/0142758 A1 | 6/2006 | Petit | |
| 2007/0129729 A1 | 6/2007 | Petit et al. | |
| 2007/0198088 A1 | 8/2007 | Biedermann et al. | |

FOREIGN PATENT DOCUMENTS

| | | |
|---|---|---|
| EP | 0669109 B1 | 5/1999 |
| EP | 1523949 A1 | 4/2005 |
| EP | 1523949 B1 | 6/2007 |
| FR | 2676911 A1 | 12/1992 |
| FR | 2696091 A1 | 4/1994 |
| FR | 2730405 A1 | 8/1996 |
| FR | 2755844 A1 | 7/2001 |
| FR | 2844180 A1 | 3/2004 |
| FR | 2867057 A1 | 9/2005 |
| FR | 2715057 A1 | 8/2008 |
| WO | 9417745 A1 | 8/1994 |
| WO | 9513756 A1 | 5/1995 |
| WO | 9519149 A1 | 7/1995 |
| WO | 9905980 A1 | 2/1999 |
| WO | 9944527 A1 | 9/1999 |
| WO | 0027297 A1 | 5/2000 |
| WO | 2004024011 A1 | 3/2004 |
| WO | 2005087121 A1 | 9/2005 |
| WO | 2006066685 A1 | 6/2006 |

* cited by examiner

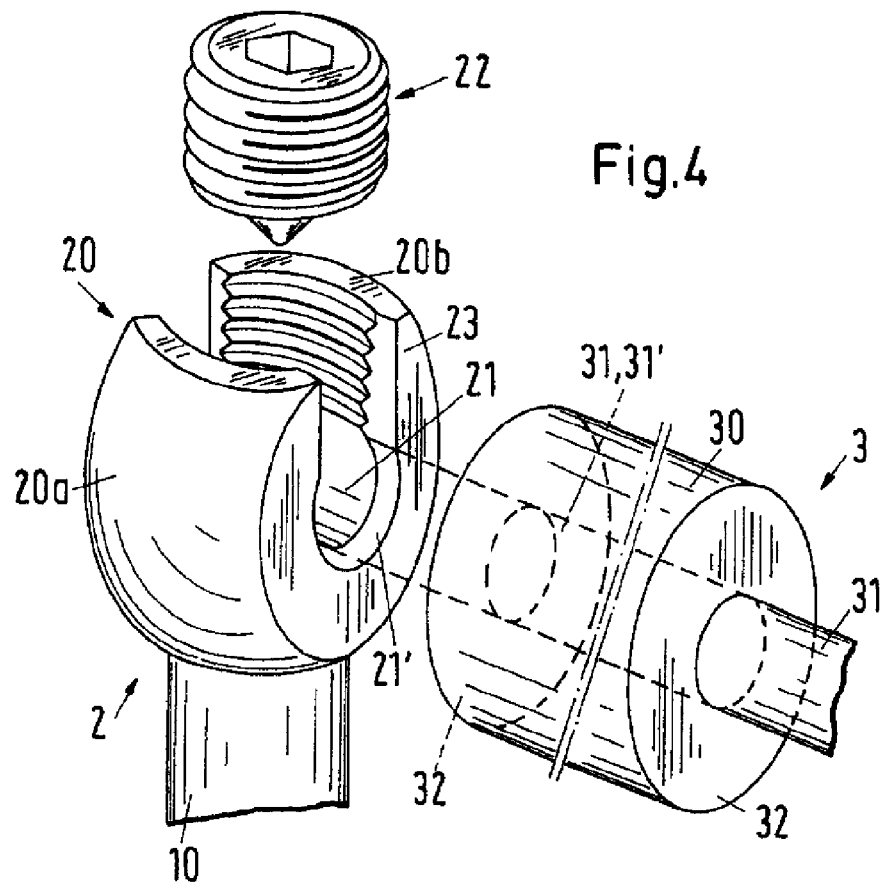
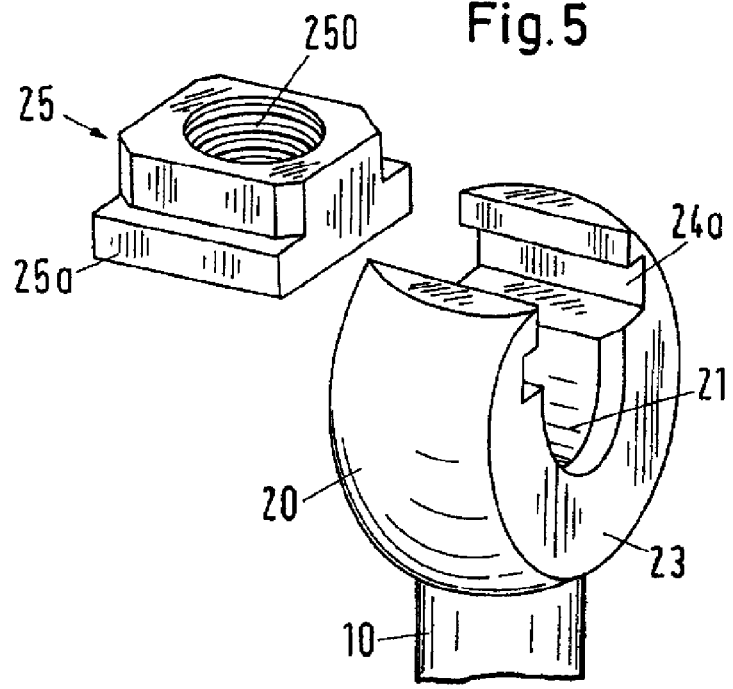

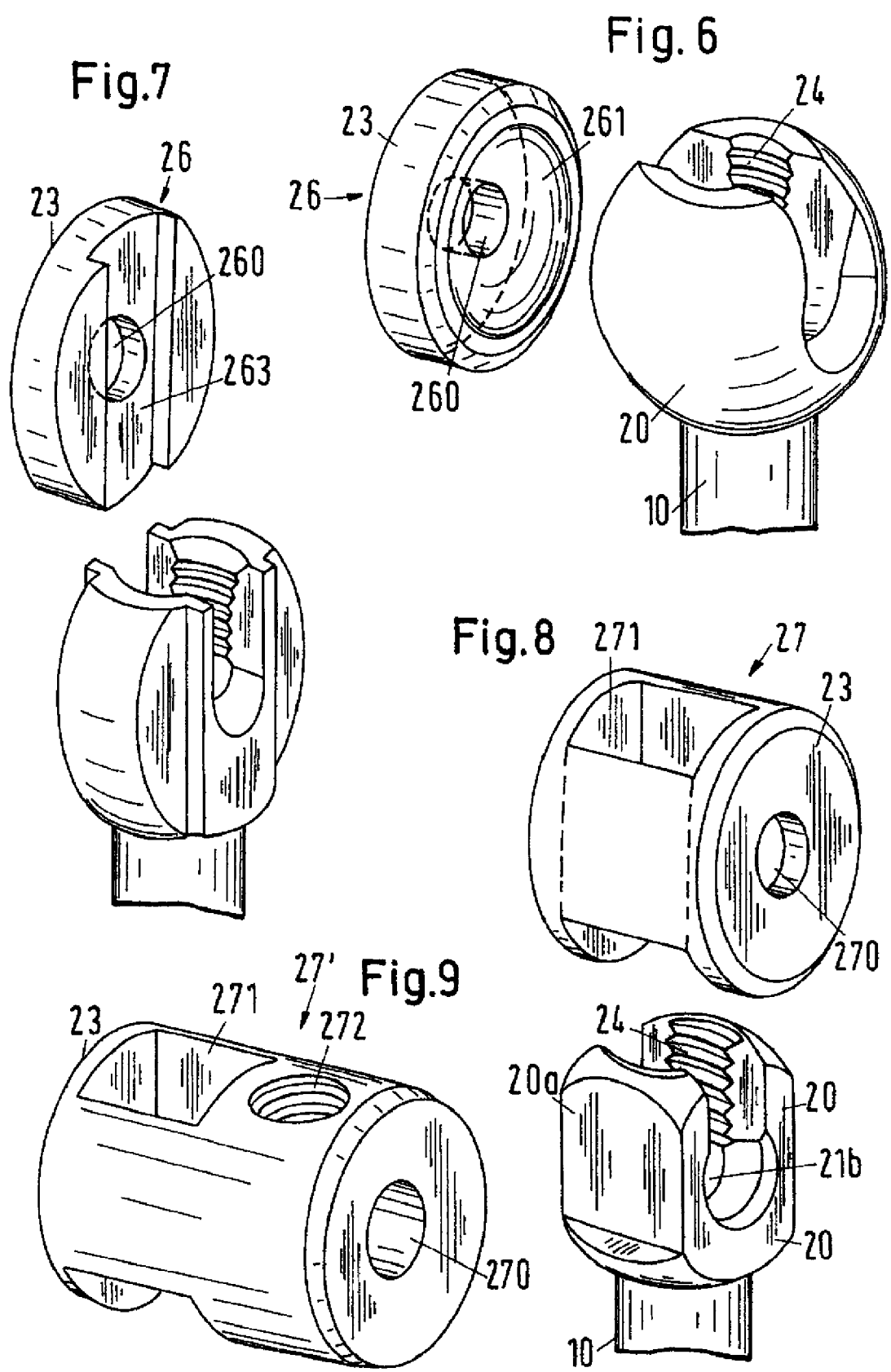

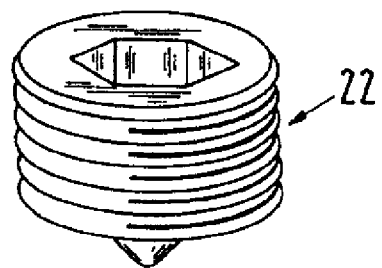
Fig.10
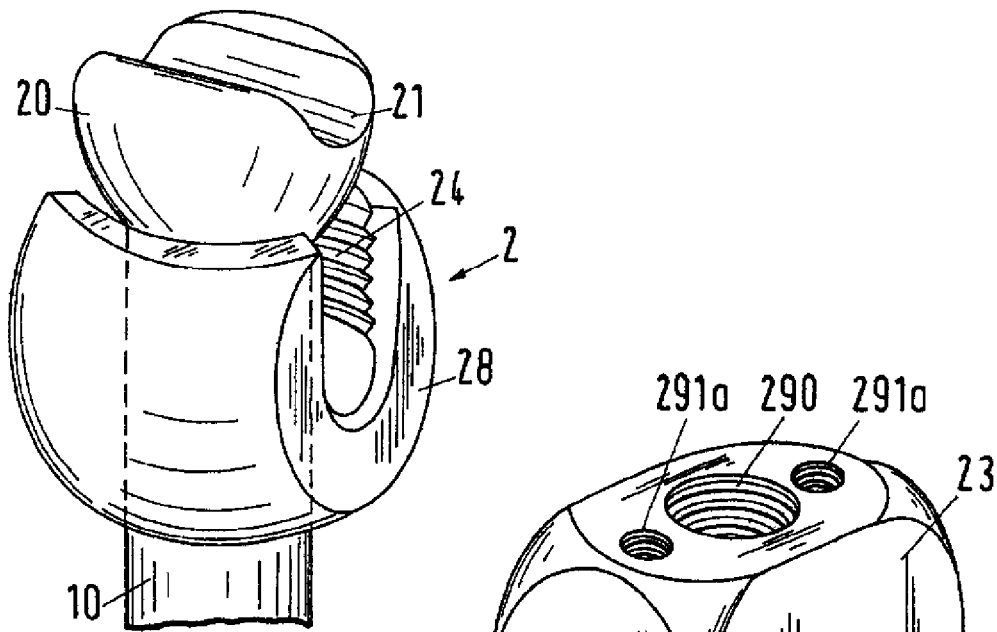
Fig.11
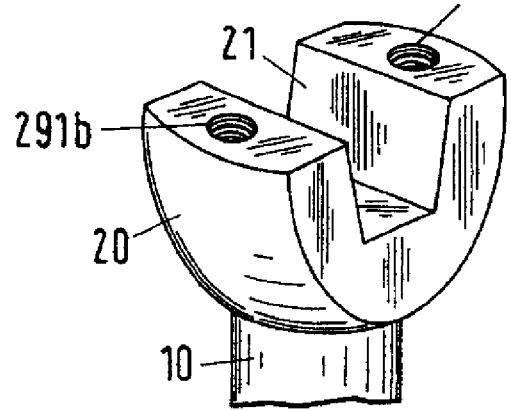

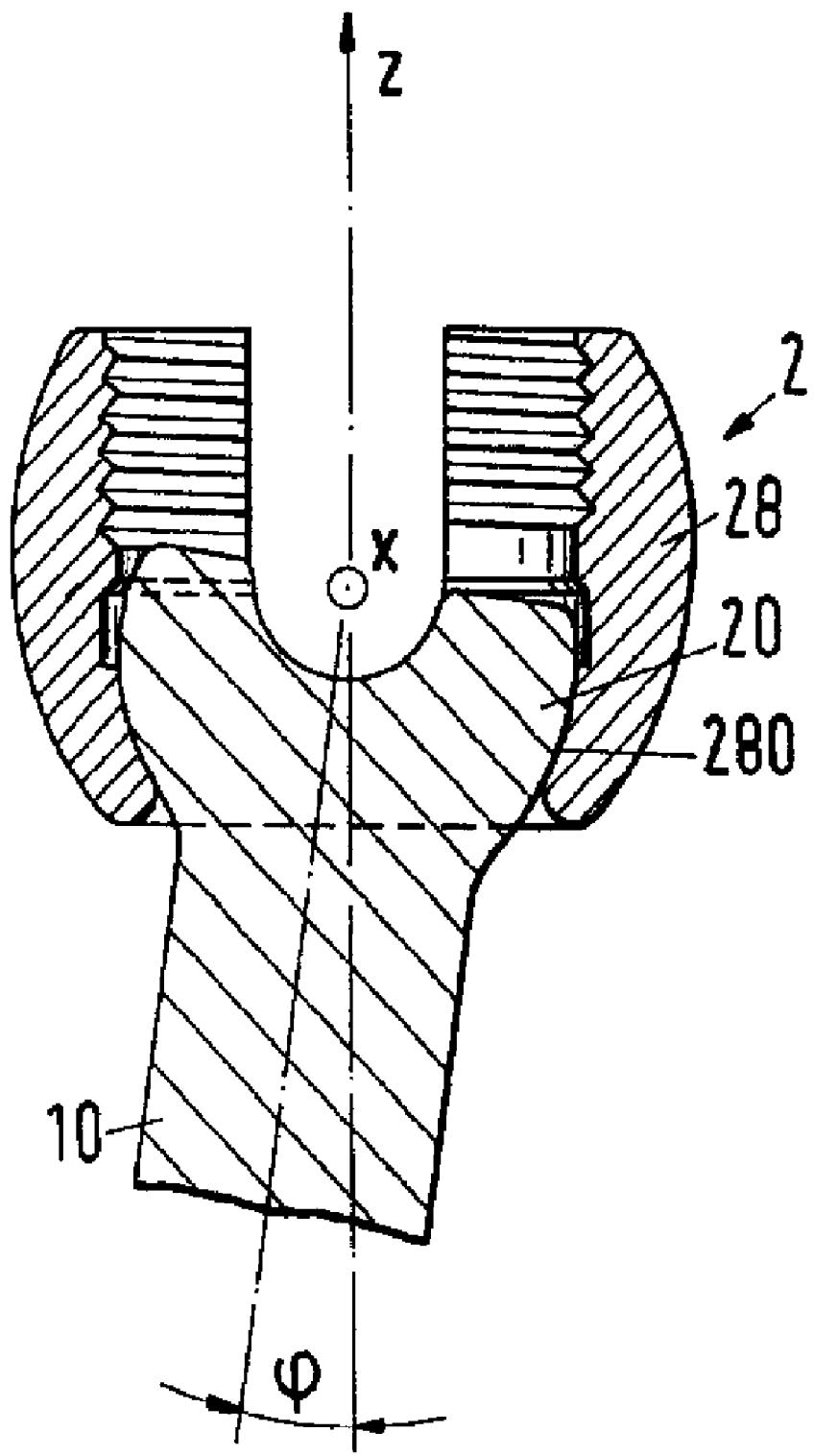

PEDICLE SCREW FOR INTERVERTEBRAL SUPPORT ELEMENTS

CROSS-REFERENCE TO RELATED APPLICATIONS

This application is a continuation of U.S. application Ser. No. 11/565,825, filed on Dec. 1, 2006; which is a continuation of U.S. application Ser. No. 09/956,055, filed on Sep. 18, 2001; which claims priority to European Patent Application No. 00810845.8, filed on Sep. 18, 2000, which are all incorporated herein by reference.

TECHNICAL FIELD

The invention relates to a pedicle screw for intervertebral support elements.

BACKGROUND

Invasive treatment methods are known for the stabilization of spinal columns in which bone bridges are made to grow between adjacent vertebral bodies using implants. Stiffening fusions of the adjacent vertebrae result through the bone bridges. In addition to stiffening operations of this kind a treatment method for stabilizing by means of an implant system is also known in which no fusion arises, but rather a mobility is preserved between adjacent vertebrae. This implant system comprises pedicle screws and intervertebral support elements which are implanted during the operation from the back. Each pedicle screw has a head which is formed as a ring. In each case two pedicle screws are screwed in a vertebral body through the pedicle passages of the vertebra. The support elements are secured at the screw heads. Two support elements which are arranged in parallel between adjacent vertebrae form a dynamic supporting of these vertebrae. The vertebrae—with the exception of the lowermost lumbar vertebra—can in each case also be connected at the same pedicle screws to an upwardly and a downwardly adjacent vertebra through two pairs of support elements.

Each support element consists of a piece of a cable-like band and a cylindrical support body which is elastically yielding. A rigid material can also be used for individual support bodies in order to stiffen the spinal column at individual locations. The band is drawn in an axial lumen of the support body. The intervertebral support elements are secured at the pedicle screws using the band. In this the bands must be drawn through through the ring heads. The drawing in of the band is an operation step which is difficult to carry out.

SUMMARY

The object of the present invention is to create, for dynamic vertebra supporting, a pedicle screw for intervertebral support elements for which the securing of the support element at the pedicle screw, which must take place during the surgical operation, can be carried out more easily.

The pedicle screw for intervertebral support elements consists of a shaft and a head which comprises at least two parts. The head is formed as a securing means for at least one support element. Each support element consists of a piece of a cable-like band and a cylindrical support body with an axial lumen which contains the band. The band can be secured outside end surfaces of the support body in the head. The head is formed with a contact surface via which a pressure stress can be exerted on the support body in the band direction, and indeed using the band and in cooperation with a further pedicle screw. A part of the head, which is firmly connected to the shaft at the one end of the latter, contains a base groove which is oriented transversally to the shaft and into which the part of the band to be secured or a connecting piece which contains the band can be introduced during the securing of the support element by means of a translatory movement in the direction of the shaft and fixed there.

BRIEF DESCRIPTION OF THE DRAWINGS

The invention will be explained in the following in more detail with reference to the drawings. Shown are.

DETAILED DESCRIPTION

Figure 1:
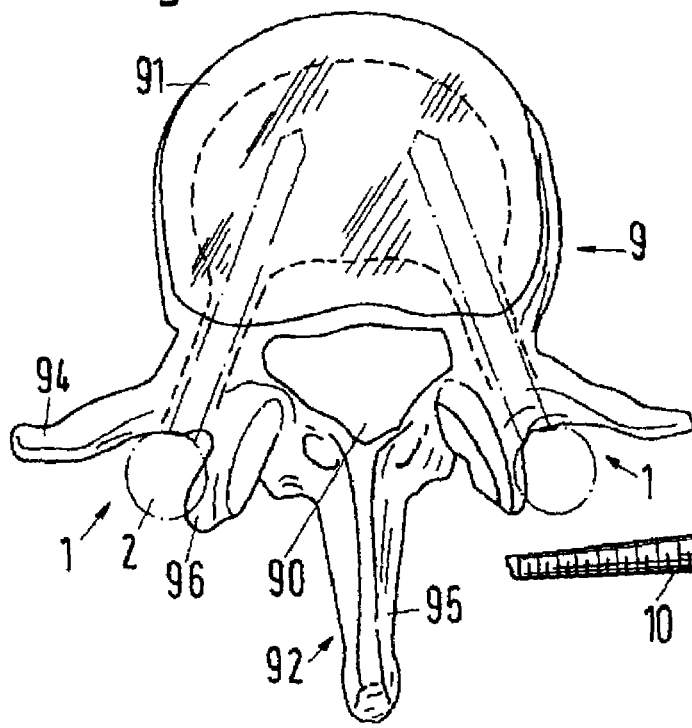
FIG. 1 a lumbar vertebra showing the position of two pedicle
Figure 2:
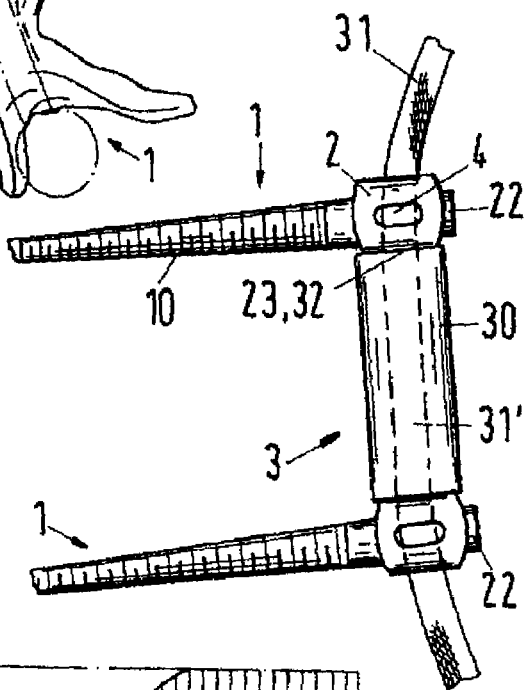
FIG. 2 two pedicle screws with an intervertebral support element for two for two adjacent vertebrae, FIG. 3 an outline illustration of adjacent lumbar vertebrae showing the position of two implanted support elements, FIG. 4 the head of a pedicle screw in accordance with the invention together with a support element, FIG. 5 a second embodiment of the head with a T-shaped groove-stone, FIGS. 6, 7 two heads in which disc-shaped parts are arranged between the support element and the head, FIG. 8 a head with a connector, FIG. 9 a variant of the connector of FIG. 8, FIG. 10 a head with a sleeve part FIG. 11 a further embodiment of the head with a connector and FIG. 12 a cross-section through the head of the embodiment in accordance with FIG. 10.

A lumbar vertebra 9 in accordance with FIG. 1 consists of a vertebral hole 90, a vertebral body 91 and a vertebral arch 92 which comprises two pedicles 93, two transverse processes 94, a spine 95 of a vertebra and articular processes 96. The positions of two pedicle screws 1 in the implanted state are indicated in chain-dotted lines. In these positions the heads 2 of the pedicle screws 1 are located directly at the outer side of the pedicles 93 between the transverse processes 94 and the articular processes 96. FIG. 2 shows two pedicle screws 1, which are provided for two adjacent vertebrae 9 and between the heads 2 of which, which are formed as rings, an intervertebral support element 3 is arranged. Shafts 10 of the pedicle screws 1 are screwed in into the vertebrae 9. The heads 2 have notches 4 laterally which are required for the implanting and orientation of the pedicle screws 1 by means of an instrument. The support element 3 consists of a piece of a cable-like band 31 and a cylindrical support body 30 in which the band 31 is contained in an axial lumen 31'. The band 31 is secured outside of end surfaces 32 of the support body 30 in each case in the heads 2 of the pedicle screws 1 with a setting screw 22. The heads 2 are provided with planar contact surfaces 23 via which a pressure stress can be exerted on the support body 30 in the band direction via their end surfaces 32, with the tension force required for this being produced using the band 31 and in cooperation with the pedicle screw 1 of the adjacent vertebra 9.

Figure 3:
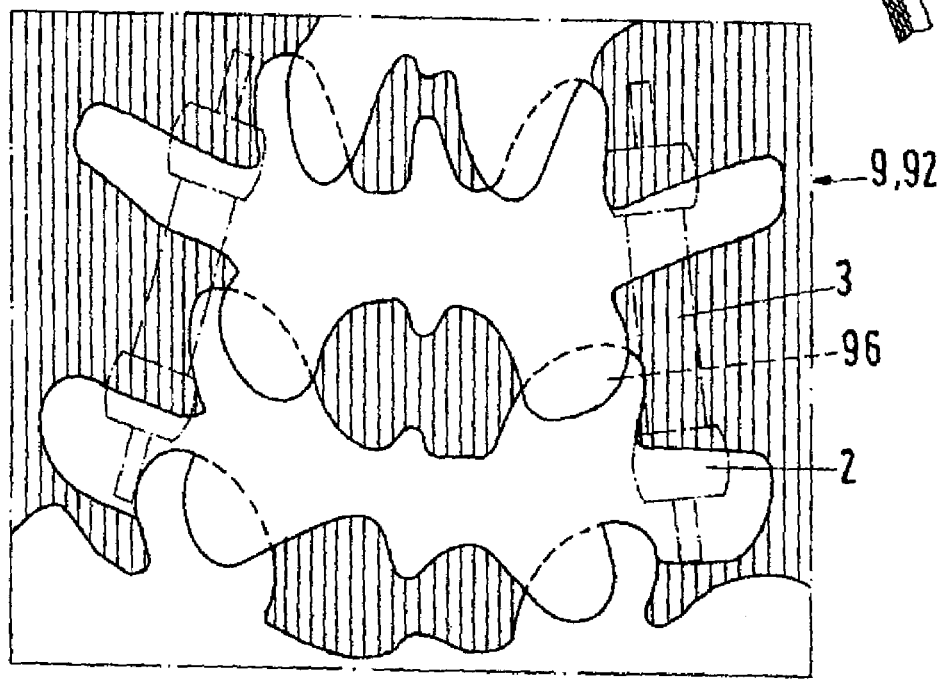

An outline drawing with two adjacent lumbar vertebrae 9 is shown in FIG. 3. The positions of two implanted support elements 3 are indicated.

The pedicle screw 1 in accordance with the invention differs from the known pedicle screw through a specially formed head 2. The support element 3 can be laid in into the latter by means of a translational movement in the direction of the shaft 2, so that the support element 3 can be fixed in the head without a drawing in of the band 31 into an eye-like securing means being required.

A first embodiment of the head 2 of a pedicle screw 1 in accordance with the invention is illustrated in FIG. 4 together with a support element 3. A part 20 of the head 2 which comprises two lugs 20a and 20b and which is firmly connected to the shaft 10 contains a base groove 21 which is oriented transversely to the shaft 10 and a thread 24. A part of the band 31 which is to be secured is inserted into the base groove 21 during the securing of the support element 3 and is fixed with a screw 22. The base groove 21 has a shape which corresponds to the shape of the band in such a manner that the base groove is formed complementarily in the insertion region. An edge region 21' of the base groove 21 can—in order to prevent a damage to the inserted band 31—be formed in such a manner that the base groove 21 widens in the direction towards the contact surface 23.

The embodiment of FIG. 4 is a first example of a pedicle screw in accordance with the invention, in which the lugs 20a, 20b, which form flanks of the base groove 21, have depressions 24 on their inner sides into which a securing part, namely the screw 22, can be firmly anchored by means of a form lock. After the production of the form lock the lugs 20a, 20b are advantageously elastically spread apart somewhat by the securing part 22, so that the position of the latter is additionally fixed as a result of an increased adhesive friction and thus of a force lock.

A second example is shown in FIG. 5, in which the lugs 20a, 20b have groove-like depressions 24a on their inner sides. A T-shaped groovestone 25 with lateral ribs 25a is pushed in between the grooves 24a after the insertion of the band 31—cf. FIG. 5—and for fixing the band 31a setting screw 22—cf. FIG. 5—is screwed into a bore in the groovestone 25 with inner thread 250.

FIGS. 6 and 7 show in each case a head 2 in which a disc-shaped part 26 is arranged between the support element 3 and the head 2. The head 2 in FIG. 6 comprises a core part 20 and at least one disc-shaped part 26 which forms the contact surface 23 to the cylindrical support body 30 of the support element 3 on the one side and which forms a contact surface 261 to the core part 20 on the other side. The surface of the core part 20 is made spherical. The contact surface 261 to the core part 20 of the disc-shaped part 26 is made in the shape of a spherical section corresponding to the shape of the core part 20. The disc-shaped part 26 is applied together with the support body 30 to the band 31, with the band 31 being drawn into the bore 260. This drawing in of the band 31 is carried out prior to the implanting of the support element 3 outside the body of the patient to be operated on.

The head 2 in FIG. 7 comprises a core part 20 which has at each end of the groove 21 an elevation 262 which is formed to fit complementarily to a groove 263 of the disc-shaped part 26 (ridge-groove form lock). The groove 263 can be pushed onto the elevation 262 in the direction of the—shaft 10. As was already the case in the example of FIG. 6, the part 26 is applied to the band 31 prior to the implanting.

FIG. 8 shows a head 2 with a core part 20 and with a connector 27 which is a sleeve-like part and the inner space of which has a square profile which is formed by planar surfaces. The core part 20 is tightly enclosed by the connector 27, so that a spreading open of the lugs 20a, 20b during the screwing in of a screw 22 (see FIG. 10) into the thread 24 is prevented.

FIG. 9 shows a variant 27' of the connector 27 of FIG. 8. This connector 27' is made longer in the direction of the groove 21 or of the bore 270 and contains a bore with inner thread 272. The band 31 can additionally be fixed below the threaded bore 272 with a second screw 22.

FIG. 10 shows a head 2 with a sleeve part 28 and with a core part 20 which is firmly connected to the one end of the shaft 10. The screw-cap part 28 is displaceable along the entire shaft 10 up to the named shaft end. In this the thread 24 comes to lie over the groove 21 so that the screw for the securing of the band 31 can be screwed into the thread 24.

FIG. 11 shows a further embodiment of the head 2 with a connector 29. The band 31 can be secured in the connector 29 in a bore 293. During the operation the connector 29, which contains the band 31, is placed onto the core part 20 of the head 2, with a connecting piece 292 of the connector 29, which has a prismatic shape, being laid in into the corresponding complementarily shaped groove 21. The securing between the connector 29 and the core part 20 can be produced for example with two screws. The non-illustrated screws are inserted through bores 291a of the connector 29 and are screwed tight in threaded bores 291b of the core part 20.

The embodiments in accordance with FIGS. 6 and 10 permit a so-called "polyaxiality" in the fixing of the support body 30 at the pedicle screws 1. The "polyaxiality" relates to the axis of the shaft 2; in all other body 30, which is given by the axis of their lumens 31'. The term "polyaxiality" is intended to mean that the angle between the two axis directions is not fixed in advance, but can vary within a certain angular range. This will be explained for the embodiment in accordance with FIG. 10 in more detail with reference to FIG. 12: FIG. 12 shows a cross-sectional illustration of the pedicle screw head 20 with the sleeve part 28, the inner surface 280 of which is a partial region of a spherical surface. The head 20 is made correspondingly spherical, so that it can be laid in into the sleeve part 28 in different positions. The axis of the shaft 10 has a main direction z perpendicular to the direction x of the support body 30 (x is perpendicular to the plane of the drawing). The shaft axis can deviate with respect to this main direction z by an angle (.phi. This angle .phi. has a maximum value .phi.sub.max which amounts to 10.degree. or even more, but which is less than 15.degree. The angle .phi. can vary in the region of a cone about the main direction z, with the half opening angle of this cone amounting to phi.sub.max. Corresponding remarks also hold for the embodiment in accordance with FIG. 6. The system for the vertebral support which can be produced with the pedicle screws in accordance with FIGS. 6 and 10 is easier to implant thanks to the "polyaxiality".

Longitudinal components comprising support elements are anchored in vertebrae with pedicle screws, with a dynamic stabilizing of the vertebrae being producible thanks to an elastic yielding of the support elements. The pedicle screws in accordance with the invention permit a head feeding of the longitudinal components. In the head feeding the longitudinal components are laid in into the heads of the pedicle screws in that merely a translational movement in the direction of the shaft in that merely a translational movement in the direction of the shaft need be carried out. Through a simple insertion of this kind the operation technique is obviously substantially simplified with respect to the older treatment methods, in which the bands of the support elements must be drawn in into the screw heads, which are formed in ring shape.

The invention claimed is:

1. A dynamic stabilization system for a spinal column, the dynamic stabilization system comprising:

a first vertebral fastener configured to be secured to a first vertebra, the first vertebral fastener including a head defining a channel;

a support element including a spacer having a bore extending therethrough and a flexible member sized to insert through the bore of the spacer; and a first member with a first portion positionable between a first surface of the spacer of the support element and a surface of the head of the first vertebral fastener, and a second portion positionable within the channel of the first vertebral fastener.

2. The dynamic stabilization system of claim 1, wherein the first member includes a third portion, wherein the first portion of the first member is positionable on a first side of the head of the first vertebral fastener and the third portion of the first member is positionable on a second side of the head of the first vertebral fastener opposite the first side of the head of the first vertebral fastener.

3. The dynamic stabilization system of claim 1, wherein the first member is configured to space the support element from direct contact with the head of the first vertebral fastener.

4. The dynamic stabilization system of claim 1, wherein the first member is positionable in abutment with the spacer.

5. The dynamic stabilization system of claim 1, wherein the first member is securable to the head of the first vertebral fastener with one or more threaded screws.

6. The dynamic stabilization system of claim 1, wherein the first member includes a bore extending therein sized to receive the flexible member.

7. The dynamic stabilization system of claim 1, wherein the first member includes a bore extending therethrough sized to receive the flexible member.

8. The dynamic stabilization system of claim 1, wherein the first member is a connector.

9. The dynamic stabilization system of claim 1, wherein the spacer is a support body.

10. The dynamic stabilization system of claim 1, wherein the first member has a longitudinal axis and the second portion of the first member is positionable in the channel of the first vertebral fastener by translation of the first member in a direction generally transverse to the longitudinal axis of the first member.

11. The dynamic stabilization system of claim 1, wherein the first vertebral fastener includes a threaded shaft portion having a longitudinal axis; and wherein the second portion of the first member is positionable in the channel of the first vertebral fastener by translation of the first member in a direction generally parallel to the longitudinal axis of the threaded shaft portion of the first vertebral fastener.

12. The dynamic stabilization system of claim 1, further comprising:

a second vertebral fastener configured to be secured to a second vertebra, the second vertebral fastener including a head defining a channel; and a second member with a first portion positionable between a second surface of the spacer of the support element and a surface of the head of the second vertebral fastener, and a second portion positionable within the channel of the second vertebral fastener.

13. The dynamic stabilization system of claim 12, wherein the second member includes a third portion, wherein the first portion of the second member is positionable on a first side of the head of the second vertebral fastener and the third portion of the second member is positionable on a second side of the head of the second vertebral fastener opposite the first side of the head of the second vertebral fastener.

14. The dynamic stabilization system of claim 12, wherein the support element is positionable between the head of the first vertebral fastener and the head of the second vertebral fastener.

15. The dynamic stabilization system of claim 12, wherein the second member is configured to space the support element from direct contact with the head of the second vertebral fastener.

16. The dynamic stabilization system of claim 12, wherein the second member is positionable in abutment with the spacer.

17. The dynamic stabilization system of claim 12, wherein the second member is securable to the head of the second vertebral fastener with one or more threaded screws.

18. The dynamic stabilization system of claim 12, wherein the second member includes a bore extending therein sized to receive the flexible member.

19. The dynamic stabilization system of claim 12, wherein the second member includes a bore extending therethrough sized to receive the flexible member.

20. The dynamic stabilization system of claim 12, wherein the second member is a connector.

21. The dynamic stabilization system of claim 12, wherein the second member has a longitudinal axis and the second portion of the second member is positionable in the channel of the second vertebral fastener by translation of the second member in a direction generally transverse to the longitudinal axis of the second member.

22. The dynamic stabilization system of claim 12, wherein the second vertebral fastener includes a threaded shaft portion having a longitudinal axis; and wherein the second portion of the second member is positionable in the channel of the second vertebral fastener by translation of the second member in a direction generally parallel to the longitudinal axis of the threaded shaft portion of the second vertebral fastener.

* * * * *